(12) United States Patent
Bergmann et al.

(10) Patent No.: US 8,252,544 B2
(45) Date of Patent: Aug. 28, 2012

(54) DIAGNOSIS AND RISK STRATIFICATION OF CARDIAC INSUFFICIENCY BY MEANS OF NATRIURETIC PEPTIDES FOR NYHA I PATIENTS

(75) Inventors: Andreas Bergmann, Berlin (DE); Nils Morgenthaler, Berlin (DE); Jana Papassotiriou, Berlin (DE); Joachim Struck, Berlin (DE); Stefan Anker, Berlin (DE)

(73) Assignee: B.R.A.H.M.S GmbH, Henningsdorf (DE)

( * ) Notice: Subject to any disclaimer, the term of this patent is extended or adjusted under 35 U.S.C. 154(b) by 402 days.

(21) Appl. No.: 12/529,365

(22) PCT Filed: Mar. 3, 2008

(86) PCT No.: PCT/DE2008/000357
§ 371 (c)(1),
(2), (4) Date: Dec. 8, 2009

(87) PCT Pub. No.: WO2008/106938
PCT Pub. Date: Sep. 12, 2008

(65) Prior Publication Data
US 2010/0143953 A1    Jun. 10, 2010

(30) Foreign Application Priority Data
Mar. 3, 2007 (DE) .................. 10 2007 010 834

(51) Int. Cl.
*G01N 31/00* (2006.01)
*G01N 33/53* (2006.01)

(52) U.S. Cl. ........ 435/7.21; 435/7.1; 436/501; 436/518; 424/9.1; 424/520; 422/50; 530/300; 530/350

(58) Field of Classification Search ........................ None
See application file for complete search history.

(56) References Cited

U.S. PATENT DOCUMENTS
| 5,498,524 A | 3/1996 | Hall |
| 2006/0234295 A1 | 10/2006 | Bergmann et al. |

FOREIGN PATENT DOCUMENTS
| EP | 0721105 B1 | 5/1999 |
| EP | 1577673 A1 | 9/2005 |
| EP | 1901073 A1 | 3/2008 |
| WO | WO-2004046181 A1 | 6/2004 |
| WO | WO-2005124364 A1 | 12/2005 |
| WO | WO-2006087373 A1 | 8/2006 |

OTHER PUBLICATIONS

Von Haehling et al., Comparison of Midregional Pro-Atrial Natriuretic Peptide with N-Terminal Pro-B-Type Natriuretic Peptide in Predicting Survival in Patients with Chronic Heart Failure. J. Am. Coil. Cardiol., 2007, 50(20):1973-80.

*Primary Examiner* — Lisa Cook
(74) *Attorney, Agent, or Firm* — Connolly Bove Lodge & Hutz LLP

(57) ABSTRACT

The invention relates to a method for the diagnosis, and/or risk stratification, and/or outcome prognosis of cardiac insufficiency for NYHA I patients, wherein a determination of the proANP marker, NT-proANP marker, or fragments or partial peptides thereof is carried out parallel to a determination of BNP, proBNP, and/or NT-proBNP on patients to be examined.

16 Claims, 1 Drawing Sheet

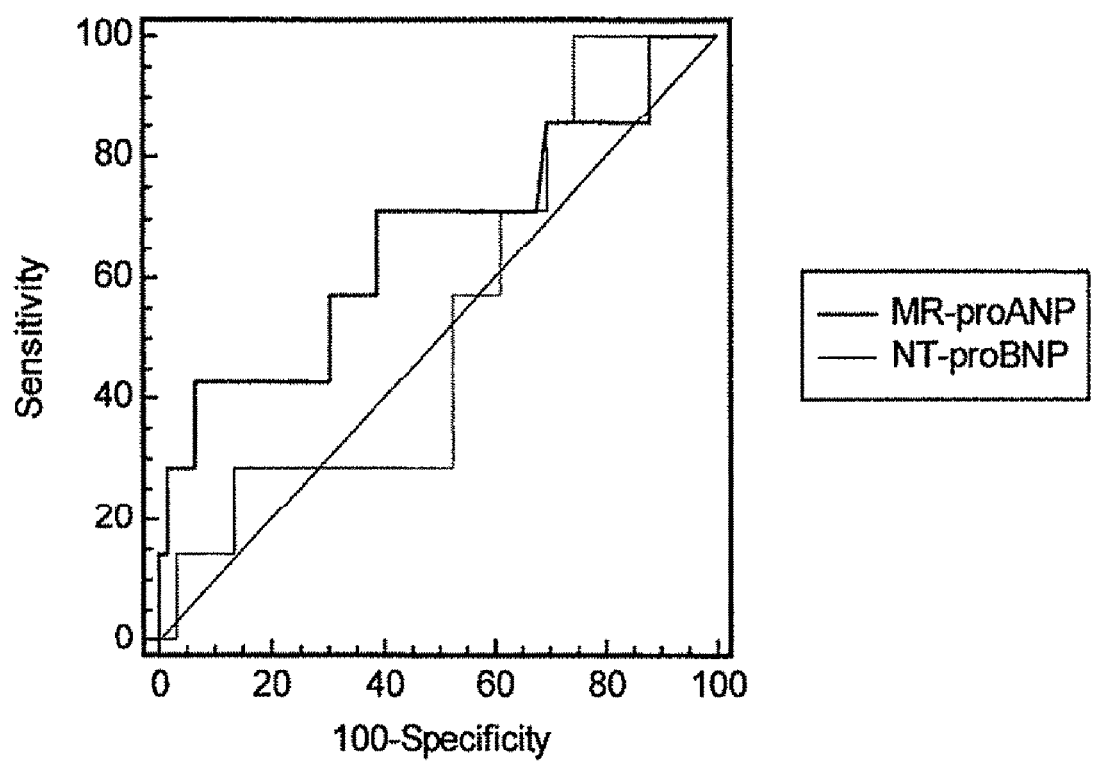

DIAGNOSIS AND RISK STRATIFICATION OF CARDIAC INSUFFICIENCY BY MEANS OF NATRIURETIC PEPTIDES FOR NYHA I PATIENTS

RELATED APPLICATIONS

This application is a national stage application under 35 U.S.C. §371 of PCT/DE2008/000357, filed Mar. 3, 2008, which claims priority of German application 102007010834.8, filed Mar. 3, 2007.

SUBMISSION OF SEQUENCE LISTING

The Sequence Listing associated with this application is filed in electronic format via EFS-Web and hereby incorporated by reference into the specification in its entirety. The name of the text file containing the Sequence Listing is SEQUENCELIST_14519-00043-US. The size of the text file is 2.54 kb; the text file was created on Aug. 31, 2009.

DESCRIPTION

The invention relates to a method for the diagnosis, and/or risk stratification, and/or outcome prognosis of cardiac insufficiency for NYHA I patients, wherein a determination of the proANP marker, or fragments or partial peptides thereof is carried out parallel to a determination of BNP, proBNP, and/or NT-proBP on patients to be examined.

In Europe, about one million patients having the symptoms of acute shortness of breath visit the emergency room of hospitals annually. Shortness of breath is a leading symptom of many diseases, and may be ascribed to heart insufficiency in approximately 35-47% of the cases (Januzzi J L Jr, Camargo C A, Anwaruddin S, Baggish A L, Chen A A, Krauser D G, Tung R, Cameron R, Nagurney J T, Chae C U, Lloyd-Jones D M, Brown D F, Foran-Melanson S, Sluss P M, Lee-Lewandrowski E, Lewandrowski K G, The N-terminal Pro-BNP investigation of dyspnea in the emergency department (PRIDE) study, Am J Cardiol. 95(8) (2005), pp. 948-954 and Maisel A S, Krishnaswamy P, Nowak R M, McCord J, Hollander J E, Duc P, Omland T, Storrow A B, Abraham W T, Wu A H, Clopton P, Steg P G, Westheim A, Knudsen C W, Perez A, Kazanegra R, Herrmann H C, McCullough P A; Breathing Not Properly Multinational Study Investigators, Rapid measurement of B-type natriuretic peptide in the emergency diagnosis of heart failure, N Engl J Med. 347(3) (2002), pp. 161-167).

In the initial stage, the patient often notices little of the heart insufficiency. Without treatment the disease increases in severity, and leads to complete physical exhaustion even while resting in the late stage. The under-supply of all bodily organs, including the heart muscle itself, may lead to death in this stage. Once the disease has advanced, life expectancy is greatly reduced, even with an optimum of therapy (approximately 30% deaths per year). It is therefore critical to recognize any cardiac insufficiency as early as possible, and to consequently address its causes.

In order to begin a suitable therapy, early diagnosis and differentiation of the underlying disease in the early stage as well as in emergency and intensive care medicine are therefore required. Due to non-specific symptoms (shortness of breath, cough) both the differentiation and delimitation of cardiac insufficiency and other diseases are often aggravated.

A test is available by means of determination of the plasma concentration of the brain natriuretic peptide (BNP or NTproBNP), which is also successfully utilized for the routine diagnosis of cardiac insufficiency (Maisel et al. (supra)). NT-proBNP is utilized according to prior art for following up cardiac insufficiencies. According to prior art proANP has also been described as a marker. U.S. Pat. No. 5,498,524 describes the use of proANP for the diagnosis of cardiac insufficiency in asymptomatic patients. EP721105B1 describes a method for determining proANP by means of suitable antibodies for heart diseases.

However, according to prior art there is a great demand for improving particularly the diagnosis, risk stratification, and outcome prognosis for patients having and indication of cardiac insufficiency.

It is therefore the object of the invention to provide a method for improved diagnosis, and/or risk stratification, and/or outcome prognosis of cardiac insufficiency.

One disadvantage of the known diagnostic methods utilizing the currently known markers is, however, that an early and complete detection of risk patients is not fully achieved, and risk stratification is therefore carried out insufficiently. A further object of the invention is to develop a method for risk stratification of cardiac insufficiency, which enables an improved detection of risk patients, especially for subgroups of patients.

Surprisingly, it has been shown that when determining proANP, or fragments or partial peptides thereof, particularly NT-proANP, or fragments or partial peptides thereof in parallel determination of proBNP, NT-proBNP, and/or RNP, an improvement of the diagnosis, risk stratification, and outcome prognosis of cardiac insufficiency can be achieved, in fact in a symptomatic cardiac insufficiency without any discomforts (NYHA stage I), particularly left cardiac insufficiency without any discomforts (NYHA stage I).

The object is therefore solved by a method according to claim 1 (hereinafter referred to as method according to the invention).

Therefore, the method according to the invention allows the improvement of the diagnostic and prognostic valence for patients of class NYHA I in a particularly advantageous manner.

In a most preferred embodiment of the invention patients further have a body mass index (BMI) of at least 30 kg/m$^2$. This is a further parameter, which additionally significantly improves the diagnostic and prognostic valence.

Within the scope of this invention "cardiac insufficiency" means an acute or chronic inability of the heart to supply sufficient blood, and as a consequence, sufficient oxygen to the tissue in order to ensure the tissue metabolism during rest or stress. From the clinical point of view, a cardiac insufficiency is present, if there are typical symptoms (dyspnea, fatigue, fluid retention), which are originally based on a cardiac functional disorder in the sense of a systolic or diastolic functional disease. The invention also comprises chronic cardiac insufficiency (CHF) (Kardiologie compact, published by Christian Mewis, Reimer Riessen, and Ioakim Spyridopoulos, 2$^{nd}$ unchanged edition, Thieme 2006). Causes of cardiac insufficiency may be: valvular defect (i.e. as a late effect of rheumatic fever), myocarditis (heart muscle inflammation), cardiac arrhythmia, heart attack, in addition to high blood pressure (hypertension), and/or arteriosclerosis (calcification) of the coronary blood vessels (coronary heart disease). The invention further comprises hypertensive heart disease with (congestive) cardiac insufficiency, hypertensive cardiac and kidney disease with (congestive) cardiac insufficiency. The present invention relates to patients having cardiac insufficiency without any discomforts (NYHA stage I). (NYHA=classification of the New York Heart Association (Hoppe U C et al.: Guidelines for the Therapy of Chronic Cardiac Insufficiency. Z Kardiol (2005) 94:488-509)).

The term "risk stratification" according to the invention comprises finding patients, particularly emergency room patients and patients at risk, having the worse prognosis for the purpose of enabling a more intensive diagnosis and therapy/treatment of cardiac insufficiency with the goal of a course that is as favorable as possible. Risk stratification according to the invention in turn allows for effective treatment methods given with regard to cardiac insufficiency without any discomforts (NYHA stage I).

Most advantageously, a safe diagnosis or outcome prognosis can be carried out by means of the method according to the invention, particularly In cases of emergency and/or intensive medicine. The method according to the invention enables clinical decisions leading to rapid therapeutic success. Such clinical decisions also comprise continuative treatments by means of medication for the treatment or therapy of cardiac insufficiency, such as ACE inhibitors, AT1 antagonists: blockers of the angiotensin-II-receptor (sub-type 1), beta blockers Bisoprolol, Carvedilol, Metoprolol, and Nebivolol, vasopressin receptor antagonists, aldosteron antagonists from NYHA stage III and up, calcium sensitizers (Levosimendan).

In a further preferred embodiment the method according to the invention therefore relates to the therapeutic control of cardiac insufficiency without any discomforts (NYHA stage I).

Therefore, the invention also relates to a method for risk stratification of patients, particularly for the stratification of patients for clinical decisions, preferably in chronologically critical intensive medicine or emergency medicine, and for the hospitalization of patients.

In a further preferred embodiment of the method according to the invention the diagnosis is carried out on the prognosis, preferably on the outcome prognosis, for the differential diagnostic early detection and detection, for the assessment of the severity, and for the therapy accompanying assessment of the course for the patients having cardiac insufficiency without any discomforts (NYHA stage I).

In a further embodiment of the method according to the invention bodily fluid, particularly blood, optionally full blood or serum, is taken from the patient to be examined, and the diagnosis is carried out in vitro/ex vivo, e.g. outside of the human or animal body. The diagnosis can be carried out based on the determination of the marker proANP, or fragments or partial peptides thereof, particularly NT-proANP, or fragments or partial peptides thereof, and the existing amount thereof in at least one patient sample. A determination of the marker proBNP, NT-proBNP, and/or RNP is carried out in parallel according to the invention, in the existing amount thereof in at least one patient sample.

The term "proANP" (also: NT-proANP) within the scope of this invention means a free polypeptide/protein of an atrial natriuretic peptide containing 98 amino acids, or fragments or partial peptides thereof. The N-terminal fragment proANP (AS 1-98) is created from the separation of the circulating hormone alpha-ANP (99-126 with 28AS) from the pro-hormone "proANP" (AS 1-126, see SEQ ID No. 1), which consists of 126 amino acids, and is stored in the secrete granules of the myoendocrinal cells, and is comprised in the invention. Furthermore, said polypeptide according to the invention may have post-translational modifications, such as glycolization, lipidization, or derivatization. Particularly NT-proANP (AS 1-98) is extremely stable in plasma.

Within the scope of this invention fragments and partial peptides may relate particularly to the mid-region of the AS 50-90 of NT-proANP (1-98) or proANP (1-126), and according to the invention a fragment or partial peptide having the AS 53-90 of the NT-proANP (1-98) (also called MR-proANP, see WO2004046181 and SEQ ID No. 1) is particularly preferred. A suitable assay is disclosed in WO2004046181A1 (BRAHMS AG). Also preferred is NT-proANP (AS 1-98). The Invention comprises the fragment (alpha)-ANP (AS 99-126).

Within the scope of this invention BNP (AS 77-108) means a B-type natriuretic peptide, which is separated from the pro-hormone proBNP (AS 1-108, see SEQ ID No. 2), wherein the NT-proBNP (AS 1-76) is simultaneously created. According to the invention NT-proBNP is preferred.

"Parallel determination" means that the determinations are particularly carried out simultaneously or at the same time, or at least allow sufficient allocation or combined evaluation.

In a further embodiment the determination of proANP, NT-proANP, or fragments or partial peptides thereof may be carried out parallel to the determination of BNP, proBNP, and/or NT-proBNP in addition with additional markers, preferably those that already indicate a cardiac insufficiency, and allow a synergetic effect of maker combinations in the method according to the invention.

Therefore, the invention relates to such an embodiment of the method according to the invention, wherein the determination is additionally selected with at least one further marker from the group of inflammatory markers, cardio-vascular markers, or ischemic markers on patients to be examined.

According to the invention the inflammatory marker may be selected from at least one marker from the group of C-reactive protein (CRP), cytokines, such as TNF-alpha, interleukins, such as IL-6, procalcitonin (1-116, 3-116), and adhesion molecules, such as VCAM or ICAM, and the cardiovascular marker may be selected from at least one marker from the group of creatine kinesis, myeloperoxidasis, copeptin, myoglobin, cardiac troponin, CRP. Furthermore, these also mean circulation regulating (pro)hormones, particularly such as pro-gastrin releasing peptide (proGRP), pro-endothelin (proEnd), pro-leptin, pro-neuropeptide-Y, pro-somatostatin, pro-neuropeptide-YY, pro-opiomelanocortin, pro-adrenomedullin (proADM), copeptine, or a partial sequence thereof.

The ischemic marker may be selected from at least one marker from the group of troponin I and T, CK-MB.

In a further embodiment of the invention the method according to the invention may be carried out by means of parallel or simultaneous determinations of the markers (i.e. multi-titer plates having 96 or more cavities), wherein the determinations are carried out on at least one patient sample.

Furthermore, the method according to the invention and the determinations thereof may be carried out on an automatic analyzer, particularly by means of a Kryptor (http://www.kryptor.net/).

In a further embodiment the method according to the invention and the determinations thereof may be carried out by means of a rapid test (e.g. lateral-flow test), preferably in a multi-parameter determination.

A further object of the invention relates the use of the markers proANP or NT-proANP, or fragments or partial peptides thereof parallel to a determination of the markers proBNP, NT-proBNP, and/or BNP on a patient to be examined for the in-vitro diagnosis, and/or risk stratification, and/or outcome prognosis of cardiac insufficiency without any discomforts (NYHA stage I). MR-proANP is a preferred fragment or partial peptide. The use according to the invention also relates to further embodiments stated above.

The following examples and figures serve for the detailed explanation of the invention, however, without limiting the invention to said examples and figures.

EXAMPLES AND FIGURES

Example 1 patients in NHYA class 1: receiver operator characteristic (ROC, StatView 5.0 software for Windows (Abacus, Concepts, Berkley, Canada, and MedCalc, Broekstraat, Mariakerke, Belgium) analyses for survival/death MR-proANP was isolated from the plasma of the patients, and frozen at −80 degrees Celsius. In order to detect MR-proANP a sandwich assay (LIA) was utilized according to WO2004046181 by BRAHMS AG (Morgenthaler et al. Immunoluminometric assay for the midregion of pro-atrial natriuretic peptide in human plasma, Clin. Chem, 2004; 50: 234-236).

NT-proBNP was determined by means of ELICIA (Roche Diagnostics, Penzberg, Germany).

Number of test persons n=66/7 patients have died.

FIG. 1 shows an area under the curve (AUC) for MR-proANP=0.665 and for NT-proBNP=0.533.

MR-proANP: 0.665-0.5 (insignificant): 0.165
NT-proBNP: 0.533-0.5 (insignificant): 0.033
0.165/0.033=5

Accordingly, this results in a diagnostic valence (consideration of survival/death) for MR-proANP that is five times higher as compared to NT-proBNP in the subgroup of patients in the NHYA class 1.

Example 2

Confirmation of the Increased Prognostic Valence of MR-proANP as Compared to NT-proBNP by Means of Cox Regression Univariate Analysis:

Approach: The median was calculated for both markers (MR-proANP and NT-proBNP) in the subgroup of the NYHA-1 patients;

This resulted in a median for NT-proBNP that is 3.7 times higher than for MR-proANP. Therefore, the RiskRatio for NT-proBNP was calculated at a concentration increase of 3.7 times that of MR-proANP in the Cox analysis.

Result of the Univariate Cox Proportional Hazard Analysis:

| Marker | ChiSquare | RiskRatio (95% CI) | P |
|---|---|---|---|
| MR-proANP (per 100 pmol/L increase) | 6.758 | 2.517 (1.255-5.047) | 0.009 |
| NT-proBNP (370 pg/ml increase) | 0.383 | 1.107 (0.803-1.525) | 0.536 |

Irrespective of the fact that no significant result was obtained for NT-proBNP (p=0.536), the risk ratio of 2.517 for MR-proANP as compared to NT-proBNP (1.107) illustrates an improvement in the subgroup of the NYHA-1 patients. A risk ratio of 1,000 shows that the risk of death per concentration unit is not increased. For MR-proANP a risk ratio of 2.517 means that the risk of death per unit (here 100 pmol/L) is increased by 151.7%. In comparison to NT-proBNP this is an increase of risk that is 14.2 times higher.

Multivariate Model:

| Marker | ChiSquare | RiskRatio (95% CI) | P |
|---|---|---|---|
| LN MR-proANP | 5.861 | 25.554 (1.854-352.272) | 0.015 |
| LN NT-proBNP | 2.093 | 0.429 (0.136-1.350) | 0.148 |
| Age | 1.673 | 0.943 (0.863-1.031) | 0.196 |

The result again shows the improvement obtained using MR-proANP, because it remains as the sole independent predictor for death in the NYHA-1 subgroup in a model with NT-proBNP and age (p=0.015).

Example 3

Patients Having a BMI$>=30$ kg/m$^2$

Analysis of the increase of the prognostic valence of MR-proANP in comparison to NT-proBNP by means of Cox regression (number of test persons: n=114; 36 patients have died)

Univariate Analysis:

Approach: The median was calculated for both markers (MR-proANP and NT-proBNP) in the subgroup of the patients having a BMI$>=30$ kg/m$^2$; this resulted in a median for NT-proBNP that is 5 times higher than for MR-proANP. Therefore, the RiskRatio for NT-proBNP was calculated at a concentration increase of 5 times that of MR-proANP in the Cox analysis.

Result of the Univariate Cox Proportional Hazard Analysis:

| Marker | ChiSquare | RiskRatio (95% CI) | P |
|---|---|---|---|
| MR-proANP (100 pmol/L increase) | 14.414 | 1.503 (1.217-1.855) | <0.0001 |
| NT-proBNP (370 pg/ml increase) | 0.662 | 1.024 (0.963-1.094) | 0.416 |

Irrespective of the fact that no significant result was obtained for NT-proBNP (p=0.416), the risk ratio of 1.503 for MR-proANP as compared to NT-proBNP (1.024) signified an advantage of the subgroup of patients having a BMI$>=30$. A risk ratio of 1,000 shows that the risk of death per concentration unit is not increased. For MR-proANP a risk ratio of 1.503 therefore means that the risk of death per unit (here 100 pmol/L) is increased by 50.3%. In comparison to NT-proBNP this is an increase of risk that is 21 times higher.

Multivariate Model:

| Marker | ChiSquare | RiskRatio (95% CI) | P |
|---|---|---|---|
| LN MR-proANP | 7.198 | 2.776 (1.317-5.854) | 0.007 |
| LN NT-proBNP | 0.005 | 0.985 (0.644-1.506) | 0.943 |

The result again shows the prognostic increase of the MR-proANP, because it remains as the sole independent predictor for death in the subgroup of patients having a BMI$>=30$ in a model with NT-proBNP (p=0.007). NT-proBNP however, is not an independent predictor.

TABLE 1

Overview of AUC for MR-proANP and NT-proBNP at various times

|  | 6 months | 12 months | 18 months | 24 months | 36 months | 48 months |
|---|---|---|---|---|---|---|
| Patients at risk | 470 | 406 | 244 | 187 | 144 | 43 |
| Patients who died | 55 | 89 | 117 | 129 | 150 | 160 |
| AUC (95% CI) | 0.75 (0.72-0.79) | 0.74 (0.70-0.78) | 0.78 (0.73-0.82) | 0.79 (0.74-0.84) | 0.79 (0.74-0.84) | 0.79 (0.74-0.84) |
| Optimum cutoff (pmol/L) | 296 | 296 | 295 | 295 | 267 | 295 |
| Sensitivity (95% CI) | 80.0 (67.0-89.6) | 74.2 (63.6-80.5) | 72.6 (63.6-80.5) | 71.3 (62.7-78.9) | 74.1 (66.0-81.2) | 68.0 (59.9-75.4) |
| Specificity (95% CI) | 63.8 (59.3-58.2) | 66.3 (61.4-70.8) | 71.5 (65.5-77.1) | 74.9 (68.0-80.9) | 71.0 (63.1-78.0) | 77.8 (70.1-84.3) |
| AUC (95% CI) | 0.74 (0.70-0.78) | 0.75 (0.71-0.79) | 0.76 (0.71-0.80) | 0.76 (0.71-0.81) | 0.75 (0.70-0.80) | 0.75 (0.69-0.80) |
| Optimum cutoff (pg/mL) | 4083 | 4046 | 4046 | 1770 | 2498 | 2015 |
| Sensitivity (95% CI) | 61.8 (47.7-74.6) | 58.4 (47.5-68.8) | 54.7 (45.2-63.9) | 76.0 (67.7-83.0) | 64.7 (53.2-72.7) | 68.0 (59.9-75.4) |
| Specificity (95% CI) | 80.0 (76.1-33.5) | 82.3 (78.2-85.9) | 85.8 (80.8-89.9) | 64.2 (56.8-71.0) | 74.2 (66.6-80.9) | 69.4 (61.2-76.8) |
| p-value (between ROCs) | 0.63 | 0.71 | 0.46 | 0.12 | 0.08 | 0.03 |

Specificity = specificity, sensitivity = sensitivity

TABLE 2

Cox Proportional Hazard Analysis for MT-proANP and NT-proBNP for predicting the survival in various stages of cardiac insufficiency

| Disease severity | NT-proBNP (per 1000 pg/mL increase) (n = 774) | | | MR-proANP (per 100 pmol/L increase) (n = 774) | | | Joint Chi Square | Added prognostic power * |
|---|---|---|---|---|---|---|---|---|
|  | Chi Square | PR (95% CI) | P | Chi Square | PR (95% CI) | P |  |  |
| NYHA I (mild) | 0.38 | 1.32 (0.55-3.13) | 0.54 | 6.76 | 2.52 (1.26-5.05) | 0.0093 | 7.16 | 1679% |
| NYHA II&III (moderate) | 70.5 | 1.11 (1.08-1.14) | 0.0001 | 105.0 | 1.19 (1.15-1.23) | 0.0001 | 106.6 | 49% |
| NYHA IV (severe) | 5.14 | 1.03 (1.00-1.05) | 0.023 | 6.65 | 1.09 (1.02-1.15) | 0.0099 | 7.77 | 29% |

* = Additional prognostic valence for MR-proANP
Number of test persons n = 774
Disease severity = severity of the disease, RR = risk ratio, increase = increase

TABLE 3

Classification by the New York Heart Association (NYHA)

| | |
|---|---|
| NYHA I | No physical limitations. Routine physical strain causes no inadequate fatigue, dysrhythmia, shortness of breath, or Angina pectoris. |
| NYHA II | Minor limitations of physical capacity. No symptoms when resting. Fatigue, dysrhythmia, shortness of breath, or Angina pectoris with routine physical strain. |
| NYHA III | Higher grade limitations of physical capacity with usual activities. No symptoms when resting. Fatigue, dysrhythmia, shortness of breath, or Angina pectoris with slight physical strain. |
| NYHA IV | Discomforts with all physical activities and while resting. Confined to bed. |

The invention claimed is:

1. A method for the in-vitro diagnosis, and/or risk stratification, and/or outcome prognosis of cardiac insufficiency without any discomforts (NYHA stage I), wherein a determination of the marker proANP or NT-proANP, or fragments or partial peptides thereof is carried out parallel to a determination of the marker proBNP, NT-proBNP, and/or BNP on patients to be examined.

2. The method for the in-vitro diagnosis, and/or risk stratification, and/or outcome prognosis of cardiac insufficiency without any discomforts (NYHA stage I) of claim 1, wherein the marker is MR-proANP (AS 53-90 of NT-proANP).

3. The method for the in-vitro diagnosis, and/or risk stratification, and/or outcome prognosis of cardiac insufficiency without any discomforts (NYHA stage I) of claim 1, wherein the patient has a body mass index of at least 30 kg/m².

4. The method for the in-vitro diagnosis, and/or risk stratification, and/or outcome prognosis of cardiac insufficiency without any discomforts (NYHA stage I), of claim 1, for making clinical decisions and for the hospitalization of patients.

5. The method for the in-vitro diagnosis, and/or risk stratification, and/or outcome prognosis of cardiac insufficiency without any discomforts (NYHA stage I), of claim 1, for the differential diagnostic early detection and detection, assessment of severity, and for therapy accompanying assessment of course.

6. The method of claim 1, wherein a determination of at least one further marker, selected from the group consisting of inflammatory markers, cardiovascular markers, and ischemic markers, is additionally carried out on a patient to be examined.

7. The method of claim 6, wherein the inflammatory marker is selected from the group consisting of C-reactive protein (CRP), cytokines, interleukins, procalcitonin (1-116, 3-116), and adhesion molecules.

8. The method of claim 6, wherein the cardiovascular marker is selected from the group consisting of creatine kinesis, myeloperoxidasis, copeptin, myoglobin, cardiac troponin, CRP, and circulation regulating (pro)hormones.

9. The method of claim 6, wherein the ischemic marker is selected from the group consisting of troponin I, troponin T and CK-MB.

10. The method of claim 1, wherein parallel or simultaneous determinations of the markers are carried out.

11. The method of claim 10, wherein the determinations are carried out on at least one patient sample.

12. The method claim 10, wherein the determinations are carried out on an automatic analyzer.

13. The method of claim 10, wherein the determinations are carried out by means of a rapid test.

14. The method of claim 4, wherein the clinical decisions relate to continuative treatment and therapy by means of medication, or intensive medicine or emergency medicine.

15. The method of claim 7, wherein the inflammatory marker is selected from the group consisting of TNF-alpha, IL-6, VCAM and ICAM.

16. The method of claim 8, wherein the cardiovascular marker is a circulation regulating (pro)hormone selected from the group consisting of pro-gastrin releasing peptide (proGRP), pro-endothelin (proEnd), pro-leptin, pro-neuropeptide-Y, pro-somatostatin, pro-neuropeptide-YY, pro-opiomelanocortin, pro-adrenomedullin (proADM), copeptine, and a partial sequence thereof.

* * * * *

SEQUENCE LISTING

<160> NUMBER OF SEQ ID NOS: 2

<210> SEQ ID NO 1
<211> LENGTH: 126
<212> TYPE: PRT
<213> ORGANISM: Homo sapiens

<400> SEQUENCE: 1

Asn Pro Met Tyr Asn Ala Val Ser Asn Ala Asp Leu Met Asp Phe Lys
1               5                   10                  15

```
Asn Leu Leu Asp His Leu Glu Glu Lys Met Pro Leu Glu Asp Glu Val
            20                  25                  30

Val Pro Pro Gln Val Leu Ser Glu Pro Asn Glu Glu Ala Gly Ala Ala
            35                  40                  45

Leu Ser Pro Leu Pro Glu Val Pro Pro Trp Thr Gly Glu Val Ser Pro
    50                  55                  60

Ala Gln Arg Asp Gly Gly Ala Leu Gly Arg Gly Pro Trp Asp Ser Ser
65                  70                  75                  80

Asp Arg Ser Ala Leu Leu Lys Ser Lys Leu Arg Ala Leu Leu Thr Ala
            85                  90                  95

Pro Arg Ser Leu Arg Arg Ser Ser Cys Phe Gly Gly Arg Met Asp Arg
            100                 105                 110

Ile Gly Ala Gln Ser Gly Leu Gly Cys Asn Ser Phe Arg Tyr
            115                 120                 125

<210> SEQ ID NO 2
<211> LENGTH: 108
<212> TYPE: PRT
<213> ORGANISM: Homo sapiens

<400> SEQUENCE: 2

His Pro Leu Gly Ser Pro Gly Ser Ala Ser Asp Leu Glu Thr Ser Gly
1               5                   10                  15

Leu Gln Glu Gln Arg Asn His Leu Gln Gly Lys Leu Ser Glu Leu Gln
            20                  25                  30

Val Glu Gln Thr Ser Leu Glu Pro Leu Gln Glu Ser Pro Arg Pro Thr
            35                  40                  45

Gly Val Trp Lys Ser Arg Glu Val Ala Thr Glu Gly Ile Arg Gly His
    50                  55                  60

Arg Lys Met Val Leu Tyr Thr Leu Arg Ala Pro Arg Ser Pro Lys Met
65                  70                  75                  80

Val Gln Gly Ser Gly Cys Phe Gly Arg Lys Met Asp Arg Ile Ser Ser
            85                  90                  95

Ser Ser Gly Leu Gly Cys Lys Val Leu Arg Arg His
            100                 105
```